United States Patent
Nagano et al.

(10) Patent No.: US 8,258,171 B2
(45) Date of Patent: Sep. 4, 2012

(54) PH-SENSITIVE FLUORESCENT PROBE

(75) Inventors: Tetsuo Nagano, Tokyo (JP); Yasuteru Urano, Kanagawa (JP); Daisuke Asanuma, Tokyo (JP)

(73) Assignee: The University of Tokyo, Tokyo (JP)

( * ) Notice: Subject to any disclaimer, the term of this patent is extended or adjusted under 35 U.S.C. 154(b) by 0 days.

(21) Appl. No.: 12/447,723

(22) PCT Filed: Nov. 15, 2007

(86) PCT No.: PCT/JP2007/072159
§ 371 (c)(1),
(2), (4) Date: Aug. 28, 2009

(87) PCT Pub. No.: WO2008/059910
PCT Pub. Date: May 22, 2008

(65) Prior Publication Data
US 2010/0068733 A1 Mar. 18, 2010

(30) Foreign Application Priority Data
Nov. 15, 2006 (JP) ................. 2006-308538

(51) Int. Cl.
*A61K 31/40* (2006.01)
*C07D 209/56* (2006.01)
(52) U.S. Cl. ......... 514/411; 548/400; 548/405; 514/408
(58) Field of Classification Search .......... 548/400, 548/405; 514/408, 411
See application file for complete search history.

(56) References Cited

U.S. PATENT DOCUMENTS

| | | | |
|---|---|---|---|
| 5,981,746 A | 11/1999 | Wolfbeis et al. | |
| 6,001,999 A | 12/1999 | Wolfbeis et al. | |
| 7,868,147 B2 * | 1/2011 | Nagano et al. | 536/18.1 |
| 7,897,786 B2 * | 3/2011 | Ulrich et al. | 548/405 |
| 2006/0275912 A1 | 12/2006 | Nagano et al. | |
| 2009/0258434 A1 | 10/2009 | Nagano et al. | |

FOREIGN PATENT DOCUMENTS

| | | |
|---|---|---|
| EP | 0881225 A2 | 12/1998 |
| JP | 10-338695 | 12/1998 |
| JP | 11-5796 | 1/1999 |
| JP | 2003-277385 | 10/2003 |
| JP | 2005-022985 A | 1/2005 |
| WO | 2004/076466 | 9/2004 |
| WO | 2007/032363 | 3/2007 |
| WO | 2008/005942 | 1/2008 |

OTHER PUBLICATIONS

Ke-Jing Huang et al., Journal of Chromatography, A, 2006, vol. 1103, No. 2, pp. 193-201.
U.S. Appl. No. 12/066,323, filed Mar. 10, 2008, entitled "Novel Maleimide Derivative."
International Search Report of International Application No. PCT/JP2007/072159.
International Preliminary Report on Patentability including the Written Opinion of International Application No. PCT/JP2007/072159.
Nagano et al., "Development of fluorescence probes for biological applications, based on photoinduced electron transfer", Bioluminescence and Chemiluminescence, Jan. 1, 2005, pp. 253-256.
Extended European Search Report issued in counterpart European Application No. 07831889 on Apr. 26, 2011.
U.S. Appl. No. 60/818,134, filed Jun. 30, 2006, Kobayashi, et al.
U.S. Appl. No. 60/922,801, filed Apr. 10, 2007, Kobayashi, et al.

\* cited by examiner

*Primary Examiner* — Golam M M Shameem
(74) *Attorney, Agent, or Firm* — Greenblum and Bernstein, P.L.C.

(57) ABSTRACT

A compound represented by the following general formula (I):

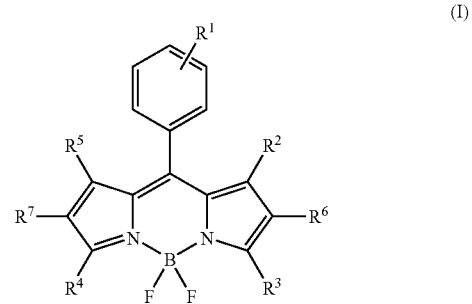

wherein $R^1$ represents an amino group which may be substituted with one or two alkyl groups; $R^2$, $R^3$, $R^4$ and $R^5$ independently represent an alkyl group; and $R^6$ and $R^7$ independently represent a monocarboxyalkyl group, a salt thereof, or an ester thereof, which is useful as a pH-sensitive fluorescent probe which emits intense fluorescence in an acidic region.

15 Claims, 1 Drawing Sheet

PH-SENSITIVE FLUORESCENT PROBE

TECHNICAL FIELD

The present invention relates to a pH-sensitive fluorescent probe. More specifically, the present invention relates to a fluorescent probe which emits intense fluorescence in an acidic region.

BACKGROUND ART

The constancy of living bodies, so-called homeostasis, is the essence of life phenomena, and among the phenomenon, the maintenance of intracellular pH is a most typical cell function. Presence of acid organelles, including lysosome as a typical example, in the cells with maintained homeostasis as described above is known for many years. It has recently been revealed that the acid organelles play important roles in various cell functions such as endocytosis, intracellular transport system, and autophagy. In order to correctly evaluate the functions of these acid organelles, a means for measuring pH, in particular, weak acidity (about pH 6) to moderate acidity (about pH 4 to 5), at specific sites where acid organelles exist in live cells has been desired. It has been attempted to develop a pH-sensitive fluorescent probe from viewpoints of high sensitivity, convenience of operation and the like. However, pH-sensitive fluorescent probes having been developed so far have a problem of decreased fluorescence intensity in an acidic region.

Various fluorescent probes for measurement of metal ions having an indacene structure have been proposed. For example, the compounds disclosed in Japanese Patent Unexamined Publication (KOKAI) No. 2005-022985 are known as fluorescent probes for zinc ion measurement having the indacene structure. However, the chemical structures of these compound are different from those of the compounds of the present invention in that they have at least one functional group for capturing zinc ion, and the aforementioned publication does not suggest nor teach that the aforementioned compounds can be used as a pH-sensitive probe. Compounds comprising the indacene structure bound with dimethylaminophenyl group are also known (Angew. Chem. Int. Ed. Engl., 36, pp. 1333-1335, 1997). However, the chemical structures of these compound are different from those of the compounds of the present invention in that they do not have carboxyl group.

Patent document 1: Japanese Patent Unexamined Publication (KOKAI) No. 2005-022985
Non-patent document 1: Angew. Chem. Int. Ed. Engl., 36, pp. 1333-1335, 1997

DISCLOSURE OF THE INVENTION

Object to be Achieved by the Invention

An object of the present invention is to provide a pH-sensitive fluorescent probe, more specifically, to provide a pH-sensitive fluorescent probe which emits intense fluorescence in an acidic region.

Means for Achieving the Object

The inventors of the present invention found that a compound, wherein the indacene structure is introduced with two carboxyalkyl groups and further introduced with an aniline derivative moiety as a moiety for detecting acidity, functioned as a fluorescent probe emitting intense fluorescence in an acidic region. This fluorescent probe is substantially non-fluorescent in a neutral to alkaline region and has high water-solubility, and therefore, can detect acid organelles in cells with excellent sensitivity. The present invention was accomplished on the basis of the aforementioned findings.

The present invention thus provides a compound represented by the following general formula (I):

[Formula 1]

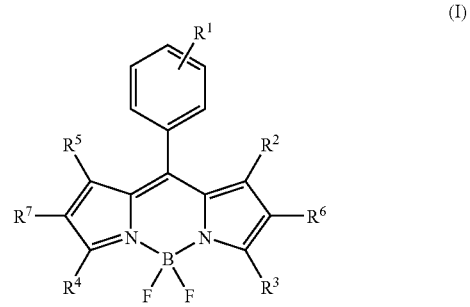

(I)

wherein $R^1$ represents an amino group which may be substituted with one or two alkyl groups (the alkyl groups may be substituted with a substituent other than amino group); $R^2$, $R^3$, $R^4$ and $R^6$ independently represent an alkyl group (the alkyl group may be substituted); and $R^6$ and $R^7$ independently represent a monocarboxyalkyl group, a salt thereof, or an ester thereof.

According to preferred embodiments of the aforementioned invention, there are provided the aforementioned compound, a salt thereof, or an ester thereof, wherein $R^1$ is an amino group which may be substituted with one or two $C_{1-4}$ alkyl groups (the alkyl groups may be substituted with carboxyl group), $R^2$, $R^3$, $R^4$ and $R^6$ are independently $C_{1-4}$ alkyl groups, and $R^6$ and $R^7$ are independently monocarboxy($C_{1-4}$)alkyl groups; the aforementioned compound, a salt thereof, or an ester thereof, wherein $R^1$ is an amino group which may be substituted with one or two $C_{1-4}$ alkyl groups, $R^2$, $R^3$, $R^4$ and $R^6$ are methyl groups, and $R^6$ and $R^7$ are independently carboxy($C_{2-3}$)alkyl groups; and the compound, a salt thereof, or an ester thereof according to claim 1, wherein $R^1$ is diethylamino group, $R^2$, $R^3$, $R^4$ and $R^6$ are methyl groups, and $R^6$ and $R^7$ are independently carboxy($C_{2-3}$)alkyl groups.

From another aspect, the present invention provides a pH-sensitive probe comprising a compound represented by the aforementioned general formula (I), a salt thereof, or an ester thereof. This pH-sensitive probe is useful for, for example, measurement of intracellular environment where acid organelles exist, and can be used for measurement of endocytosis and the like.

The present invention also provides a method for measuring an acidic region in a cell, which comprises the following steps:
(a) the step of introducing a compound represented by the aforementioned general formula (I), a salt thereof, or an ester thereof into a cell, and
(b) the step of measuring fluorescence emitted by the compound represented by the aforementioned general formula (I) or a salt thereof in the cell. By this method, for example, an intracellular acidic region where acid organelles exist can be measured.

The present invention further provides a biological substance labeled with a compound represented by the aforementioned general formula (I).

BEST MODE FOR CARRYING OUT THE INVENTION

Figure 1:
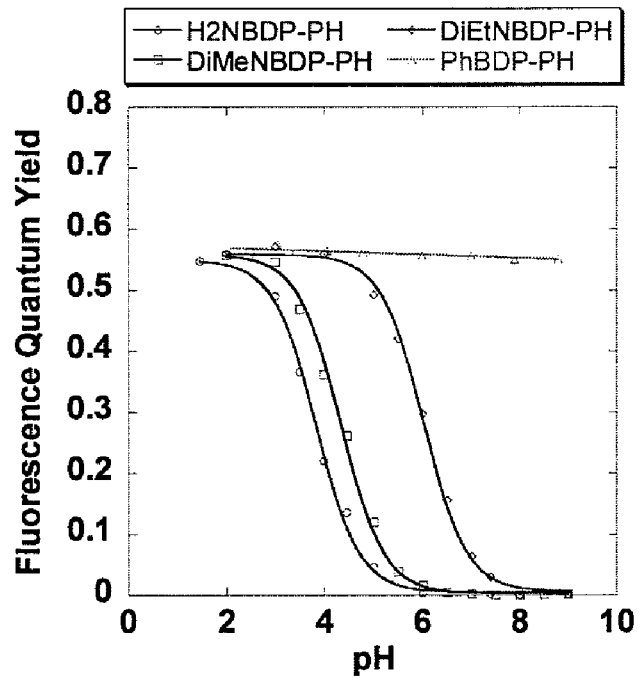
FIG. 1 shows relationship of pH and fluorescence intensity (fluorescence quantum yield) of the compounds 3a, 3b and 3c of the present invention and the control compound 3d (indicated as H2NBDP-PH, DiMeNBDP-PH, DiEtNBDP-PH and PhBDP-PH in the graph, respectively).

In the specification, "an alkyl group" or an alkyl moiety of a substituent containing the alkyl moiety (for example, an alkylcarbonyl group and the like) means, for example, a linear, branched, or cyclic alkyl group, or an alkyl group consisting of a combination thereof, having 1 to 12 carbon atoms, preferably 1 to 6 carbon atoms, more preferably 1 to 4 carbon atoms. Preferred examples of the alkyl group include a lower alkyl group (an alkyl group having 1 to 6 carbon atoms) such as methyl group, ethyl group, n-propyl group, isopropyl group, cyclopropyl group, n-butyl group, sec-butyl group, isobutyl group, tert-butyl group, cyclopropylmethyl group, n-pentyl group, n-hexyl group, and the like. The same shall apply to the alkyl moiety of other substituents having an alkyl moiety (alkoxyl group).

In the specification, when "which may be substituted" is referred to for a certain functional group, the type, number, and substitution position of the substituent are not particularly limited, unless specifically indicated. The functional group may have, for example, a halogen atom (any of fluorine atom, chlorine atom, bromine atom, and iodine atom), hydroxy group, amino group, carboxy group, sulfo group, an alkyl sulfonate group, or the like as the substituent.

In the aforementioned general formula (I), $R^1$ represents unsubstituted amino group or an amino group substituted with one or two alkyl groups. When the amino group is substituted with two alkyl groups, they may be the same or different. The alkyl groups substitute on the amino group may be substituted (provided that amino group is excluded from the substituent). For example, the alkyl group may have a substituent such as carboxyl group. As the alkyl group, a $C_{1-4}$ alkyl group is preferred. Examples of $R^1$ include, for example, unsubstituted amino group, monomethylamino group, dimethylamino group, monomethylamino group, ethylmethylamino group, diethylamino group, mono-n-propylamino group, n-propylmethylamino group, carboxy-substituted ethylamino group and the like, but not limited to these examples. Among them, dimethylamino group, methylethylamino group and diethylamino group are preferred, methylethylamino group and diethylamino group are still more preferred, and diethylamino group is especially preferred. Although the position of $R^1$ substituting on the benzene ring is not particularly limited, $R^1$ is preferably on the para-position.

As the alkyl group represented by $R^2$, $R^3$, $R^4$ and $R^5$, a $C_{1-4}$ alkyl group is preferred, and methyl group is particularly preferred. As the monocarboxyalkyl group represented by $R^6$ and $R^7$, an alkyl group substituted with one carboxyl group at the end of the alkyl group is preferred, and for example, a monocarboxy($C_{1-4}$) alkyl group and the like are preferred. Particularly preferred are monocarboxyethyl group, monocarboxypropyl group, and the like.

The compounds of the present invention represented by the formula (I) may exist as a an acid addition salt or base addition salt. Examples of the acid addition salt include, for example, mineral acid salts such as hydrochloride, sulfate, and nitrate, and organic acid salts such as methanesulfonate, p-toluenesulfonate, oxalate, citrate and tartrate. Examples of the base addition salt include metal salts such as sodium salt, potassium salt, calcium salt, and magnesium salt, ammonium salt, and organic amine salts such as triethylamine salt. In addition, the compounds may form a salt with an amino acid such as glycine. The compounds of the present invention or salts thereof may exist as hydrates or solvates, and all these substances fall within the scope of the present invention.

The compounds of the present invention represented by the aforementioned general formula (I) can also be made into esters. For example, the compounds of the present invention can be made into succinimidyl esters, and thereby a labeling function to a protein and the like can be imparted. By using these esters, biological substances (for example, proteins, antibodies and the like) labeled with the compounds of the present invention represented by the aforementioned general formula (I) can be prepared. Alternatively, by converting the compounds of the present invention into alkyl esters such as methyl ester or an ester of alkyl ether such as methoxymethyl ester, higher incorporation property of the compounds into a cell is achievable. After the incorporation into a cell, such esters can be hydrolyzed by an action of intracellular esterase to regenerate the compounds represented by the aforementioned general formula (I), and efficient measurement of an intracellular acidic region or acid organelles can be performed.

The compounds of the present invention represented by the aforementioned general formula (I) may have one or more asymmetric carbon depending on type of substituent. Any of stereoisomers such as optical isomers based on one or more asymmetric carbon atoms, and diastereoisomers based on two one or more asymmetric carbon atoms, as well as arbitrary mixtures of stereoisomers, racemates, and the like fall within the scope of the present invention.

The preparation methods of typical compounds among the compounds of the present invention are specifically shown in examples of the specification. Therefore, those skilled in the art can prepare any of the compounds of the present invention represented by the aforementioned general formula (I) by suitably choosing starting materials, reaction conditions, reagents, and the like on the basis of these explanations, and modifying or altering these methods as required. Synthetic methods of the indacene structure are mentioned in, for example, Japanese Patent Unexamined Publication (KOKAI) Nos. 10-338695 and 11-5796, as well as in New J. Chem., 25, pp. 289-292, 2001; Tetrahedron Letters, 42, pp. 6711-6713, 2001; Angew. Chem. Int. Ed., 40 pp. 385-387, 2001; Japanese Patent Application No. 2002-80230, and the like, and therefore, those skilled in the art can prepare the compounds of the present invention still more easily by referring to these publications. The entire disclosures of the aforementioned publications are incorporated in the disclosures of the specification by reference.

The compounds of the present invention represented by the aforementioned general formula (I) are useful as a pH-sensitive fluorescent probe. The compounds of the present invention represented by the aforementioned general formula (I) or salts thereof have a characteristic that they are substantially non-fluorescent in a neutral to basic region or only weakly fluorescent, whilst they emit intense fluorescence in an acidic region. Therefore, the compounds of the present invention represented by the aforementioned general formula (I) or salts thereof are extremely useful as a pH-sensitive fluorescent probe for measuring an acidic region in a living cell or living tissue under the physiological conditions. Changes of a pH profile corresponding to change of the amino group represented by $R^1$ are specifically shown in the examples. For example, by using the compounds of the present invention or salts thereof as a pH-sensitive probe, pH of a specific region in a cell where acid organelles exist can be correctly measured. For example, the presence of acid organelles in cells, including lysosome as a typical example, is known for many years, and it has recently been elucidated that the acid organelles play important roles in various cell functions such as endocytosis, intracellular transport system, and autophagy. Therefore, endocytosis can be measured by using the pH-sensitive probe of the present invention. The pH sensitivity of the compounds of the present invention or salts thereof can be suitably chosen by changing type of the substituent represented by $R^1$, i.e., unsubstituted amino group or amino group substituted with one or two alkyl groups. Accordingly, a compound having appropriate pH sensitivity can be easily chosen depending on a purpose. The term "measurement" used in this specification should be construed in the broadest sense thereof including quantitative measurement and qualitative measurement.

The method for using the pH-sensitive fluorescent probe of the present invention is not particularly limited, and the probe can be used in the same manner as that for conventionally known fluorescent probes. Generally, a compound represented by the aforementioned general formula (I) or a salt thereof may be dissolved in an aqueous medium such as physiological saline or a buffer, or in a mixture of an aqueous medium and a water-miscible solvent such as ethanol, acetone, ethylene glycol, dimethyl sulfoxide, and dimethylformamide, the resultant solution may be added to a suitable buffer containing cells or tissues, and then the fluorescence spectra may be measured. The pH-sensitive fluorescent probe of the present invention may be used in the form of a composition in combination with appropriate additives. For example, the probe can be combined with additives including buffers, dissolving aids and pH adjusters.

EXAMPLES

The present invention will be more specifically explained with reference to examples. However, the scope of the present invention is not limited by the following examples. The compound numbers used in the example correspond to the compound numbers used in the following scheme.

[Formula 2]

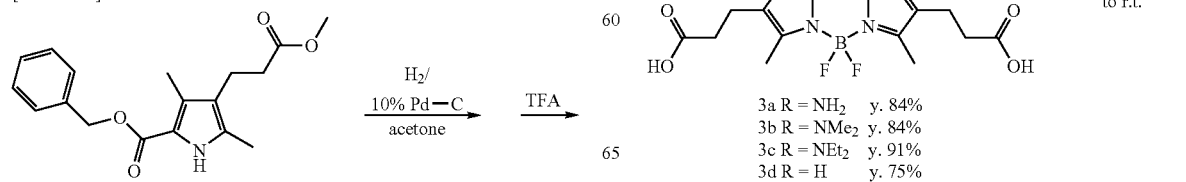

-continued

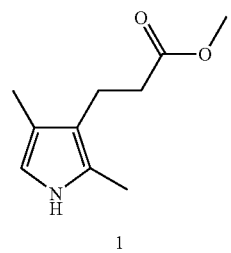

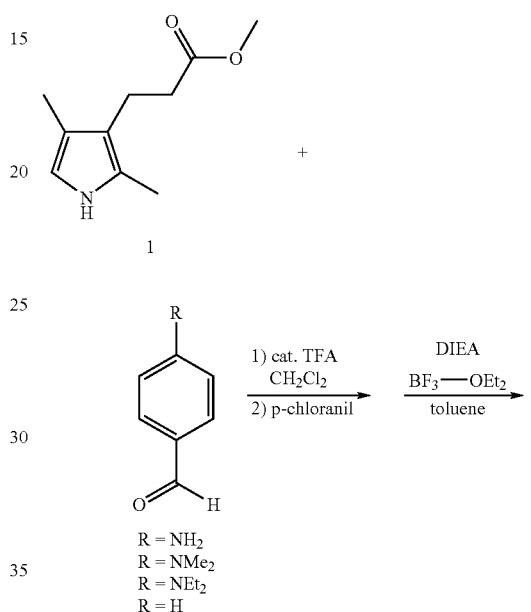

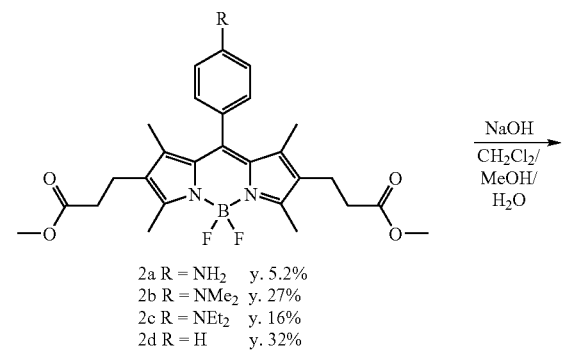

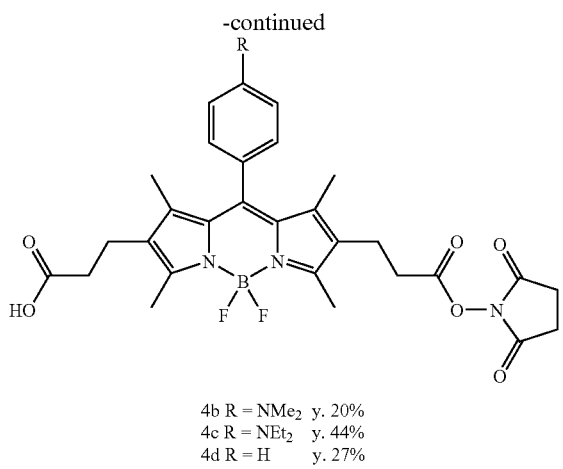

4b R = NMe₂   y. 20%
4c R = NEt₂   y. 44%
4d R = H      y. 27%

Example 1

(1) Methyl 2,4-dimethyl-3-pyrrolepropionate (1)

Methyl 5-(benzoyloxy-carbonyl)-2,4-dimethyl-3-pyrrolepropionate (1.55 g, 4.91 mmol) was dissolved in acetone (150 mL) containing 10% palladium/carbon, and the mixture was stirred at room temperature for 12 hours under a hydrogen atmosphere. The reaction mixture was filtered, the solvent was evaporated under reduced pressure, then the residue was immediately dissolved in trifluoroacetic acid (TFA, 10 mL), and the mixture was stirred at room temperature for 10 minutes under an argon atmosphere. The reaction mixture was added with dichloromethane (30 mL), then washed successively with water and 1 mol/L aqueous sodium hydrogencarbonate, dried over anhydrous sodium sulfate, and evaporated under reduced pressure to obtain pale brown oil (1, 0.835 g, 94%).

$^1$H NMR (300 MHz, CDCl$_3$) δ 2.02 (s, 3H, NHCHCCH$_3$), 2.16 (s, 3H, NHCCH$_3$), 2.42-2.48 (m, 2H, COCH$_2$), 2.69-2.74 (m, 2H, COCH$_2$CH$_2$), 3.66 (s, 3H, OCH$_3$), 6.36 (s, 1H, NHCH), 7.64 (br s, 1H, NH).
$^{13}$C NMR (75 MHz, CDCl$_3$) δ 10.2, 11.1, 19.9, 35.3, 51.4, 113.0, 116.5, 117.7, 124.1, 173.9.
LRMS (ESI$^+$) m/z 182 [M+H]$^+$.

(2) 1,3,5,7-Tetramethyl-2,6-bis-(2-methoxycarbonylethyl)-8-(4-aminophenyl)-4,4-difluoro-4-bora-3a,4a-diaza-s-indacene (2a)

The compound 1 (0.542 g, 2.99 mmol) and 4-aminobenzaldehyde (0.153 g, 1.49 mmol) were dissolved in dichloromethane (300 mL) containing a catalytic amount of TFA, and the mixture was stirred overnight at room temperature under an argon atmosphere. The mixture was added with tetrachloro-1,4-benzoquinone (p-chloranil, 0.361 g, 1.47 mmol), and the mixture was further stirred for 10 minutes. The reaction mixture was washed with water, dried over anhydrous sodium sulfate, and evaporated under reduced pressure, and the resulting residue was repeatedly purified by alumina column chromatography using dichloromethane/methanol (9:1) containing 1% triethylamine (TEA) as elution solvent to obtain reddish and greenish solid. The resulting solid was dissolved in toluene (100 mL) containing N,N-diisopropylethylamine (DIEA, 3 mL), the solution was slowly added dropwise with trifluoroborane etherate (BF$_3$.OEt$_2$, 3 mL) at room temperature with stirring, and then the mixture was stirred for 10 minutes. The reaction mixture was washed with water, dried over anhydrous sodium sulfate, and evaporated under reduced pressure, and the resulting residue was purified by silica gel column chromatography using dichloromethane/methanol (95:5) as elution solvent to obtain red solid (2a, 40.1 mg, 5.2%).

$^1$H NMR (300 MHz, CDCl$_3$) δ 1.41 (s, 6H, NCCCH$_3$), 2.33-2.28 (m, 4H, COCH$_2$), 2.53 (s, 6H, NCCH$_3$), 2.61-2.67 (m, 4H, COCH$_2$CH$_2$), 3.65 (s, 6H, OCH$_3$), 3.93 (br s, 2H, NH$_2$), 6.76-6.78 (m, 2H, NH$_2$CCHCH), 6.96-6.99 (m, 2H, NH$_2$CCH).
$^{13}$C NMR (75 MHz, CDCl$_3$) δ 12.0, 12.4, 19.2, 34.2, 51.5, 115.3, 124.7, 128.7, 128.9, 131.4, 139.5, 141.8, 147.1, 153.4, 173.0.
HRMS (ESI$^+$) Calcd for [M+Na]$^+$ m/z 534.23516, Found 534.23846 (Δ 3.30 mmu).

(3) 1,3,5,7-Tetramethyl-2,6-bis-(2-carboxyethyl)-8-(4-aminophenyl)-4,4-difluoro-4-bora-3a,4a-diaza-s-indacene (3a)

The compound 2a (40.1 mg, 78.4 μmol) was dissolved in dichloromethane (1 mL), the solution was added successively with methanol (20 mL) and 1 mol/L aqueous sodium hydroxide (5 mL), and the mixture was stirred overnight at room temperature. The reaction mixture was added with water (30 mL), the mixture was washed with dichloromethane, and then added with 1 mol/L hydrochloric acid (about 5 mL) under UV (365 nm) irradiation until the solution started to emit green fluorescence to make the solution acidic. The mixture was extracted with dichloromethane, then the organic layer was dried over anhydrous sodium sulfate, and evaporated under reduced pressure, and the resulting residue was purified twice by semi-preparative HPLC under the following conditions: A/B=50/50 (0 min) to 0/100 (20 min), then A/B=70/30 (0 min) to 0/100 (30 min) (solvent A: H$_2$O, 0.1% TFA, solvent B: acetonitrile/H$_2$O=80/20, 0.1% TFA). An aqueous solution of the fraction containing the objective compound was extracted with dichloromethane, and then the organic layer was dried over anhydrous sodium sulfate, and evaporated under reduced pressure to obtain orange solid (3a, 32.0 mg, 84%).

$^1$H NMR (300 MHz, CD$_3$OD) δ 1.37 (s, 6H, NCCCH$_3$), 2.24 (t, 4H, J=7.4, 8.0 Hz, COCH$_2$), 2.38 (s, 6H, NCCH$_3$), 2.54 (t, 4H, J=7.4, 8.0 Hz, COCH$_2$CH$_2$), 6.73-6.75 (m, 2H, NCCHCH), 6.83-6.86 (m, 2H, NCCH).
$^{13}$C NMR (75 MHz, CD$_3$OD) δ 12.5, 12.7, 20.3, 35.3, 116.6, 125.2, 130.1, 130.4, 132.7, 140.8, 144.0, 150.2, 154.6, 176.5.
HRMS (ESI$^+$) Calcd. for [M+Na]$^+$ m/z 506.20386, Found 506.20729 (Δ 3.43 mmu).

(4) 1,3,5,7-Tetramethyl-2,6-bis-(2-methoxycarbonylethyl)-8-[4-(N,N-dimethylamino)phenyl]-4,4-difluoro-4-bora-3a,4a-diaza-s-indacene (2b)

The compound 1 (0.574 g, 3.17 mmol) and 4-(N,N-dimethylamino)benzaldehyde (0.236 g, 1.58 mmol) were dissolved in dichloromethane (300 mL) containing a catalytic amount of TFA, and the mixture was stirred at room temperature for one day under an argon atmosphere. The mixture was added with p-chloranil (0.384 g, 1.56 mmol), and the mixture was further stirred for 10 minutes. The reaction mixture was washed with water, dried over anhydrous sodium sulfate, and evaporated under reduced pressure, and the resulting residue was repeatedly purified by alumina column chromatography using dichloromethane/methanol (9:1) containing 1% TEA as elution solvent to obtain greenish solid. The resulting solid was dissolved in toluene (100 mL) containing DIEA (5 mL), the mixture was slowly added dropwise with $BF_3 \cdot OEt_2$ (5 mL) at room temperature with stirring, and then the mixture was stirred for 10 minutes. The reaction mixture was washed with water, dried over anhydrous sodium sulfate, and evaporated under reduced pressure, and the resulting residue was purified three times by silica gel column chromatography using dichloromethane/methanol (#1 97:3; #2 99:1; #3 100:0) as elution solvent to obtain brown solid (3a, 228 mg, 27%).

$^1$H NMR (300 MHz, $CDCl_3$) δ 1.40 (s, 6H, $NCCCH_3$), 2.33-2.38 (m, 4H, $COCH_2$), 2.53 (s, 6H, $NCCH_3$), 2.61-2.67 (m, 4H, $COCH_2CH_2$), 3.02 (s, 6H, $NCH_3$), 3.65 (s, 6H, $OCH_3$), 6.75-6.80 (m, 2H, NCCHCH), 7.01-7.06 (m, 2H, NCCH).

$^{13}$C NMR (75 MHz, $CDCl_3$) δ 12.1, 12.5, 19.4, 34.3, 40.3, 51.6, 112.4, 122.5, 128.7, 128.8, 131.6, 139.6, 142.4, 150.7, 153.3, 173.1.

HRMS ($ESI^+$) Calcd. for $[M+Na]^+$ m/z 562.26646, Found 562.26315 (Δ −3.32 mmu).

(5) 1,3,5,7-Tetramethyl-2,6-bis-(2-carboxyethyl)-8-[4-(N,N-dimethylamino)phenyl]-4,4-difluoro-4-bora-3a,4a-diaza-s-indacene (3b)

The compound 2b (50.8 mg, 94.2 μmol) was dissolved in dichloromethane (1 mL), the solution was added successively with methanol (20 mL) and 1 mol/L aqueous sodium hydroxide (5 mL), and the mixture was stirred at room temperature for 2 hours. The reaction mixture was added with water (30 mL), the mixture was washed with dichloromethane, and then added with 1 mol/L hydrochloric acid (about 5 mL) under UV (365 nm) irradiation until the solution started to emit green fluorescence to make the solution acidic. The mixture was extracted with dichloromethane, then the organic layer was dried over anhydrous sodium sulfate, and evaporated under reduced pressure, and the resulting residue was purified by semi-preparative HPLC under the following conditions: A/B=60/40 (0 min) to 0/100 (30 min) (solvent A: $H_2O$, 0.1% TFA, solvent B: acetonitrile/$H_2O$=80/20, 0.1% TFA). An aqueous solution of the fraction containing the objective compound was extracted with dichloromethane, and then the organic layer was dried over anhydrous sodium sulfate, and evaporated under reduced pressure to obtain red solid (3b, 40.3 mg, 84%).

$^1$H NMR (300 MHz, $CD_3OD+DMF-d_7$) δ 1.34 (s, 6H, $NCCCH_3$), 2.21-2.26 (m, 4H, $COCH_2$), 2.39 (s, 6H, $NCCH_3$), 2.51-2.56 (m, 4H, $COCH_2CH_2$), 2.91 (s, 6H, $NCH_3$), 6.77-6.80 (m, 2H, NCCHCH), 6.94-6.97 (m, 2H, NCCH).

$^{13}$C NMR (75 MHz, $CD_3OD+DMF-d_7$) δ 12.6, 12.8, 20.3, 35.3, 40.5, 113.6, 123.5, 130.1, 130.6, 132.7, 140.8, 143.9, 152.5, 154.6, 175.9.

HRMS ($ESI^-$) Calcd. for $[M-H]^-$ m/z 510.23757, Found 510.23776 (Δ 0.19 mmu).

(6) 1,3,5,7-Tetramethyl-2-(2-carboxyethyl)-6-(2-succinimidyloxycarbonylethyl)-8-[4-(N,N-dimethylamino)-phenyl]-4,4-difluoro-4-bora-3a,4a-diaza-s-indacene (4b)

The compound 3b (11.1 mg, 21.7 μmol) was dissolved in N,N-dimethylformamide (DMF, 2 mL). The solution was added successively with a 100 mmol/L solution of N-hydroxysuccinimide (NHS) in DMF and a 100 mmol/L solution of water-soluble carbodiimide (WSCD) in DMF (32.6 μmol each) under ice cooling, and the mixture was stirred for 24 hours with gradually returning the mixture to room temperature. The solvent was evaporated under reduced pressure, and the residue was purified by semi-preparative HPLC under the following conditions: A/B=50/50 (0 min) to 0/100 (20 min) (solvent A: $H_2O$, 0.1% TFA, solvent B: acetonitrile/$H_2O$=80/20, 0.1% TFA). An aqueous solution of the fraction containing the objective compound was extracted with dichloromethane, and then the organic layer was dried over anhydrous sodium sulfate, and evaporated under reduced pressure to obtain red solid (4b, 2.6 mg, 20%). Yield based on the starting material: 41%.

HRMS ($ESI^+$) Calcd for $[M+Na]^+$ m/z 631.25154, Found 631.25518 (Δ 3.64 mmu).

(7) 1,3,5,7-Tetramethyl-2,6-bis-(2-methoxycarbonylethyl)-8-[4-(N,N-diethylamino)phenyl]-4,4-difluoro-4-bora-3a,4a-diaza-s-indacene (2c)

The compound 1 (0.542 g, 2.99 mmol) and 4-(N,N-diethylamino)benzaldehyde (0.265 g, 1.49 mmol) was dissolved in dichloromethane (300 mL) containing a catalytic amount of TFA, and the mixture was stirred overnight at room temperature under an argon atmosphere. The mixture was added with p-chloranil (0.370 g, 1.51 mmol), and the mixture was further stirred for 10 minutes. The reaction mixture was washed with water, dried over anhydrous sodium sulfate, and evaporated under reduced pressure, and the resulting residue was purified three times by alumina column chromatography using dichloromethane/methanol (#1 95:5; #2 98:2; #3 100:0) containing 1% TEA as elution solvent to obtain greenish solid. The resulting solid was dissolved in toluene (100 mL) containing DIEA (5 mL), the solution was slowly added dropwise with $BF_3 \cdot OEt_2$ (5 mL) at room temperature with stirring, and then the mixture was stirred for 10 minutes. The reaction mixture was washed with water, dried over anhydrous sodium sulfate, and evaporated under reduced pressure, and the resulting residue was purified three times by silica gel column chromatography using dichloromethane/methanol (#1 98:2; #2 100:0; #3 95:5) as elution solvent to obtain orange solid (2c, 136 mg, 16%).

$^1$H NMR (300 MHz, $CDCl_3$) δ 1.22 (t, 6H, J=7.0 Hz, $NCH_2CH_3$), 1.44 (s, 6H, $NCCCH_3$), 2.36 (t, 4H, J=7.3, 8.4 Hz, $COCH_2$), 2.53 (s, 6H, $NCCH_3$), 2.65 (t, 4H, J=7.3, 8.4 Hz, $COCH_2CH_2$), 3.41 (q, 4H, J=7.0 Hz, $NCH_2$), 3.65 (s, 6H, $OCH_3$), 6.74 (d, 2H, J=8.6 Hz, NCCHCH), 6.99 (d, 2H, J=8.6 Hz, NCCH).

$^{13}$C NMR (75 MHz, $CDCl_3$) δ 12.1, 12.3, 12.5, 19.3, 34.3, 44.3, 51.6, 112.0, 121.6, 128.6, 129.0, 131.7, 139.6, 142.6, 148.2, 153.1, 173.1.

HRMS ($ESI^+$) Calcd for $[M+H]^+$ m/z 568.31582, Found 568.31626 (Δ 0.44 mmu).

(8) 1,3,5,7-Tetramethyl-2,6-bis-(2-carboxyethyl)-8-[4-(N,N-diethylamino)phenyl]-4,4-difluoro-4-bora-3a,4a-diaza-s-indacene (3c)

The compound 2c (136 mg, 239 μmol) was dissolved in dichloromethane (3 mL), the solution was added successively with methanol (20 mL) and 1 mol/L aqueous sodium hydroxide (5 mL), and the mixture was stirred at room temperature for 4 hours. The reaction mixture was added with water (30 mL), the mixture was washed with dichloromethane, and then added with 1 mol/L hydrochloric acid (about 5 mL) under UV (365 nm) irradiation until the solution started to emit green fluorescence to make the solution acidic. The mixture was extracted with dichloromethane, then the organic layer was dried over anhydrous sodium sulfate, and evaporated under reduced pressure, and the resulting compound was purified by preparative TLC using dichloromethane/acetone (1:1) as developing solvent to obtain orange solid (3c, 118 mg, 91%).

$^1$H NMR (300 MHz, CD$_3$OD) δ 1.10 (t, 6H, J=7.0 Hz, NCH$_2$CH$_3$), 1.39 (t, 6H, NCCCH$_3$), 2.25 (t, 4H, J=7.5, 7.9 Hz, COCH$_2$), 2.39 (s, 6H, NCCH$_3$), 2.56 (t, 4H, J=7.5, 7.9 Hz, COCH$_2$CH$_2$), 3.33 (q, 4H, J=7.0 Hz, NCH$_2$), 6.75 (d, 2H, J=8.8 Hz, NCCHCH), 6.93 (d, 2H, J=8.8 Hz, NCCH).

$^{13}$C NMR (75 MHz, CD$_3$OD) δ 12.5, 12.7, 20.4, 35.3, 45.4, 113.3, 122.8, 130.3 (representing two different carbons), 132.8, 140.8, 144.2, 149.7, 154.4, 176.5.

HRMS (ESI$^-$) Calcd for [M−H]$^-$ m/z 538.26887, Found 538.26446 (Δ−4.40 mmu).

(9) 1,3,5,7-Tetramethyl-2-(2-carboxyethyl)-6-(2-succinimidyloxycarbonylethyl)-8-[4-(N,N-diethylamino)-phenyl]-4,4-difluoro-4-bora-3a,4a-diaza-s-indacene (4c)

The compound 3c (25.7 mg, 47.6 lima was dissolved in DMF (2 mL). The solution was added successively with a 100 mmol/L solution of NHS in DMF and a 100 mmol/L solution of WSCD in DMF (47.6 μmol each) under ice cooling, and the mixture was stirred for 14 hours with gradually returning the mixture to room temperature. The solvent was evaporated under reduced pressure, and the residue was purified by preparative TLC using dichloromethane/acetone (1:1) as developing solvent to obtain red solid (4c, 13.4 mg, 44%).

HRMS (ESI$^+$) Calcd. for [M+H]$^+$ m/z 637.30090, Found 637.30278 (Δ 1.89 mmu).

(10) 1,3,5,7-Tetramethyl-2,6-bis-(2-methoxycarbonylethyl)-8-phenyl-4,4-difluoro-4-bora-3a,4a-diaza-s-indacene (2d)

The compound 1 (0.634 g, 3.50 mmol) and benzaldehyde (0.185 g, 1.74 mmol) were dissolved in dichloromethane (300 mL) containing a catalytic amount of TFA, and the mixture was stirred overnight at room temperature under an argon atmosphere. The mixture was added with p-chloranil (0.428 g, 1.74 mmol), and the mixture was further stirred for 10 minutes. The reaction mixture was washed with water, dried over anhydrous sodium sulfate, and evaporated under reduced pressure, and the resulting compound was repeatedly purified by alumina column chromatography using dichloromethane containing 1% TEA as elution solvent to obtain green solid. The resulting solid was dissolved in toluene (100 mL) containing DIEA (5 mL), the solution was slowly added dropwise with BF$_3$.OEt$_2$ (5 mL) at room temperature with stirring, and then the mixture was stirred for 10 minutes. The reaction mixture was washed with water, dried over anhydrous sodium sulfate, and evaporated under reduced pressure, and the resulting residue was purified by silica gel column chromatography using dichloromethane as elution solvent to obtain orange solid (2d, 273 mg, 32%).

$^1$H NMR (300 MHz, CDCl$_3$) δ 1.29 (s, 6H, NCCCH$_3$), 2.32-2.38 (m, 4H, COCH$_2$), 2.54 (s, 6H, NCCH$_3$), 2.61-2.66 (m, 4H, COCH$_2$CH$_2$), 3.65 (s, 6H, OCH$_3$), 7.25-7.28 (m, 2H, benzene), 7.46-7.49 (m, 3H, benzene).

$^{13}$C NMR (75 MHz, CDCl$_3$) δ 11.8, 12.6, 19.3, 34.2, 51.6, 128.0, 128.9, 129.1, 130.9, 135.4, 139.4, 140.9, 154.0, 173.0.

HRMS (ESI$^+$) Calcd. for [M+Na]$^+$ m/z 519.22426, Found 519.22433 (Δ 0.07 mmu).

(11) 1,3,5,7-Tetramethyl-2,6-bis-(2-carboxyethyl)-8-phenyl-4,4-difluoro-4-bora-3a,4a-diaza-s-indacene (3d)

The compound 2d (40.1 mg, 78.4 lima was dissolved in dichloromethane (1 mL), the solution was added successively with methanol (20 mL) and 1 mol/L aqueous sodium hydroxide (5 mL), and the mixture was stirred overnight at room temperature. The reaction mixture was added with water (30 mL), the mixture was washed with dichloromethane, and then added with 1 mol/L hydrochloric acid (about 5 mL) under UV (365 nm) irradiation until the solution started to emit green fluorescence to make the solution acidic. The mixture was extracted with dichloromethane, then the organic layer was dried over anhydrous sodium sulfate, and evaporated under reduced pressure, and the resulting residue was purified by semi-preparative HPLC under the following conditions: A/B=50/50 (0 min) to 0/100 (20 min), then A/B=70/30 (0 min) to 0/100 (30 min) (solvent A: H$_2$O, 0.1% TFA, solvent B: acetonitrile/H$_2$O=80/20, 0.1% TFA). An aqueous solution of the fraction containing the objective compound was extracted with dichloromethane, and then the organic layer was dried over anhydrous sodium sulfate, and evaporated under reduced pressure to obtain red solid (3d, 32.0 mg, 84%).

$^1$H NMR (300 MHz, CD$_3$OD) δ 1.19 (s, 6H, NCCCH$_3$), 2.23 (t, 4H, J=8.1 Hz, COCH$_2$), 2.40 (s, 6H, NCCH$_3$), 2.55 (t, 4H, J=8.1 Hz, COCH$_2$CH$_2$), 7.21-7.46 (m, 5H, benzene).

$^{13}$C NMR (75 MHz, CD$_3$OD/NaOD) δ 12.2 (representing two different carbons), 22.0, 39.3, 129.5, 130.2, 130.4, 132.0, 132.2, 136.9, 140.4, 142.1, 155.2, 181.8.

HRMS (ESI$^+$) Calcd for [M+Na]$^+$ m/z 491.19296, Found, 491.18910 (Δ−3.87 mmu)

(12) 1,3,5,7-Tetramethyl-2-(2-carboxyethyl)-6-(2-succinimidyloxycarbonylethyl)-8-phenyl-4,4-difluoro-4-bora-3a,4a-diaza-s-indacene (4d)

The compound 3d (12.4 mg, 26.5 pimp was dissolved in DMF (2 mL). The solution was added successively with a 100 mmol/L solution of NHS in DMF and a 100 mmol/L solution of WSCD in DMF (39.7 μmol each) under ice cooling, and the mixture was stirred for 24 hours with gradually returning the mixture to room temperature. The solvent was evaporated under reduced pressure, and the residue was purified by semi-preparative HPLC under the following conditions: A/B=50/50 (0 min) to 0/100 (20 min) (solvent A: H$_2$O, 0.1% TFA, solvent B: acetonitrile/H$_2$O=80/20, 0.1% TFA). An aqueous solution of the fraction containing the objective compound was extracted with dichloromethane, and then the organic layer was dried over anhydrous sodium sulfate, and evaporated under reduced pressure to obtain red solid (4d, 4.0 mg, 27%). Yield based on the starting material: 24%.

HRMS (ESI$^-$) Calcd for [M−H]$^-$ m/z 564.21175, Found 564.21392 (Δ 2.18 mmu).

Example 2

Optical Characteristics of pH-Sensitive Fluorescent Probe of the Present Invention and pH-Dependent Change Thereof Optical characteristics of the compounds of the present invention, 3a (H$_2$NBDP-PH), 3b (DiMeNBDP-PH), and 3c (DiEtNBDP-PH), and a compound not having an anilinic amino group as a pH detecting moiety, 3d (PhBDP-PH), as a control compound were measured. The results are shown in Table 1. It was found that the compounds 3a, 3b and 3c gave pH-dependency following the Henderson-Hasselbach equation, and they functioned as a pH-sensitive probe (FIG. 1). All the compounds were substantially non-fluorescent in a neutral to alkaline environment, and had a weakly acidic to moderately acidic pKa, and the deprotonated compounds were protonated in an acidic region to give fluorescence quantum yields increased 250 to 300 times.

TABLE 1

| Compound | Form | $\lambda_{abs,max}$ [nm] | $\lambda_{em,max}$ [nm] | Stokes' shift [nm] | $\epsilon$ [M$^{-1}$cm$^{-1}$] | $\Phi_{fl}^{c}$ | pK$_a^d$ |
|---|---|---|---|---|---|---|---|
| 3a | N-protonated[a] | 520 | 533 | 13 | 72100 | 0.55 | 3.8 |
|  | N-nonprotonated[b] | 519 | 536 | 17 | 71100 | 0.002 |  |
| 3b | N-protonated[a] | 521 | 535 | 14 | 58900 | 0.56 | 4.3 |
|  | N-nonprotonated[b] | 519 | 535 | 16 | 62300 | 0.002 |  |
| 3c | N-protonated[a] | 521 | 534 | 13 | 64100 | 0.56 | 6.0 |
|  | N-nonprotonated[b] | 519 | 536 | 17 | 64400 | 0.002 |  |
| 3d | — | 520 | 534 | 14 | 73200 | 0.56 | — |

[a]Measured at pH 1.47 for 3a and at pH 2.00 for 3b and 3c
[b]Measured at pH 9.00 for 3a, 3b, and 3c
[c]Calculated by using fluorescein ($\Phi_{fl}$ = 0.85) as reference
[d]Determined with Henderson-Hasselbach equation using fluorescence quantum yield

Example 3

In order to impart a function for labeling a protein and the like to the compounds of the present invention, the compounds 4b and 4c were synthesized wherein one of the two carboxyl groups was replaced with succinimidyl (NHS) ester. The compound 4d not having an anilinic amino group was synthesized as a control compound.

Figure 2:
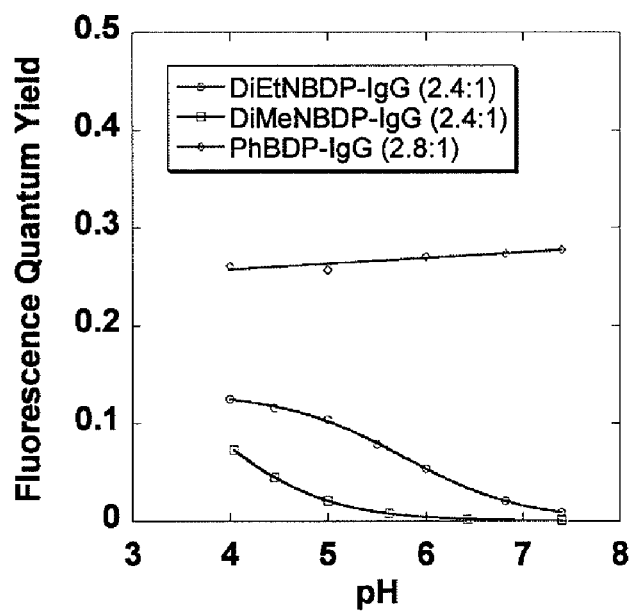
FIG. 2 shows relationship of pH and fluorescence intensity (fluorescence quantum yield) of antibodies labeled with the compound 3b or 3c of the present invention, or the control compound 3d (indicated as DiMeNBDP-IgG, DiEtNBDP-IgG, and PhBDP-IgG all in the graph, respectively).

IgG was labeled with 4b and 4c, as well as 4d as a control by the following method to obtain DiMeNBDP-IgG, DiEtN-BDP-IgG, and PhBDP-IgG, respectively. As IgG, a marketed humanized monoclonal antibody therapeutic agent, Herceptin (registered trademark), was used. Herceptin was dissolved in 200 mmol/L sodium phosphate buffer (pH 8.37, NaPi buffer) to prepare a 1.0 mg/mL Herceptin/NaPi solution. The compound 4b, 4c or 4d was added to 1.0 mL of the 1.0 mg/mL Herceptin/NaPi solution. The mixture was left standing for 1 hour under light shielding, and labeled IgG was isolated by using PD 10 column (GE Healthcare) with PBS (pH 7.4, GIBCO) as elution solution. Fluorescence of DiMeNBDP-IgG and DiEtNBDP-IgG increased when the solution became more acidic, in the same manner as the compounds 3b and 3c, whereas PhBDP-IgG as the control gave no change of fluorescence with the change of pH (FIG. 2).

The followings features were confirmed from the results of Examples 2 and 3 mentioned above.
(1) By appropriately choosing the amino group represented by R$^1$ of the compounds of the present invention, a pH change in a desired pH range in an acidic region can be measured with suitable fluorescence intensity. Therefore, the compounds of the present invention are useful as a pH-sensitive probe.
(2) It is generally considered that pH of acid organelles is about 6.5 to 6.0 for early endosomes, about 6.0 to 5.0 for late endosomes, or about 4.8 to 4.5 for lysosomes. Fluorescence intensity of the compounds of the present invention changes in these pH ranges in a pH-dependent manner, and therefore, they are useful as a pH-sensitive probe for measurement of an acidic region where intracellular acid organelles exist.
(3) Biological substances (protein, IgG and the like) can be labeled with the compounds of the present invention without degrading the pH sensitivity thereof. By suitably choosing a biological substance to be labeled, cell functions in which acid organelles are involved such as endocytosis, intracellular transport system and autophagy can be measured.
(4) Although selection of the amino group represented by R$^1$ in the compounds of the present invention depends on the pH range to be measured, the compounds 3c and 4c wherein R$^1$ is diethylamino group, for example, are especially useful, because they enable measurement of pH change of acid organelles over a wide pH range with high sensitivity.

INDUSTRIAL APPLICABILITY

The compounds of the present invention are useful as a pH-sensitive fluorescent probe which emits intense fluorescence in an acidic region.

What is claimed is:

1. A compound represented by the following formula (I):

[Formula 1]

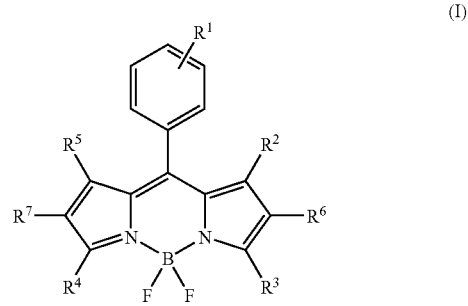

(I)

wherein R$^1$ represents an amino group which may be substituted with one or two alkyl groups (the alkyl groups may be substituted with a substituent other than amino group); R$^2$, R$^3$, R$^4$ and R$^5$ independently represent an alkyl group (the alkyl group may be substituted); and R$^6$ and R$^7$ independently represent a monocarboxyalkyl group, a salt thereof, or an ester thereof.

2. The compound, a salt thereof, or an ester thereof according to claim 1, wherein R$^1$ is an amino group which may be substituted with one or two C$_{1-4}$ alkyl groups (the alkyl groups may be substituted with carboxyl group), R$^2$, R$^3$, R$^4$ and R$^5$ are independently C$_{1-4}$ alkyl groups, and R$^6$ and R$^7$ are independently monocarboxy(C$_{1-4}$)alkyl groups.

3. The compound, a salt thereof, or an ester thereof according to claim 1, wherein R$^1$ is an amino group which may be substituted with one or two C$_{1-4}$ alkyl groups, R$^2$, R$^3$, R$^4$ and R$^5$ are methyl groups, and R$^6$ and R$^7$ are independently carboxy(C$_{2-3}$)alkyl groups.

4. The compound, a salt thereof, or an ester thereof according to claim 1, wherein R$^1$ is diethylamino group, R$^2$, R$^3$, R$^4$ and R$^5$ are methyl groups, and R$^6$ and R$^7$ are independently carboxy(C$_{2-3}$)alkyl groups.

5. A pH-sensitive probe comprising the compound represented by the formula (I), a salt thereof, or an ester thereof according to claim 1.

6. The pH-sensitive probe according to claim 5, which is used for measurement of an acidic region where intracellular acid organelles exist.

7. The pH-sensitive probe according to claim 5, which is used for measurement of endocytosis.

8. A method for measuring an acidic region in a cell, which comprises the following steps:
   (a) the step of introducing the compound represented by the formula (I), a salt thereof, or an ester thereof according to claim 1 into a cell, and
   (b) the step of measuring fluorescence emitted by the compound represented by the formula (I) or a salt thereof in the cell.

9. The method according to claim 8, which is for measurement of an acidic region where intracellular acid organelles exist.

10. A pH-sensitive probe comprising the compound represented by the formula (I), a salt thereof, or an ester thereof according to claim 2.

11. A pH-sensitive probe comprising the compound represented by the formula (I), a salt thereof, or an ester thereof according to claim 3.

12. A pH-sensitive probe comprising the compound represented by the formula (I), a salt thereof, or an ester thereof according to claim 4.

13. A method for measuring an acidic region in a cell, which comprises the following steps:
   (a) the step of introducing the compound represented by the formula (I), a salt thereof, or an ester thereof according to claim 2 into a cell, and
   (b) the step of measuring fluorescence emitted by the compound represented by the formula (I) or a salt thereof in the cell.

14. A method for measuring an acidic region in a cell, which comprises the following steps:
   (a) the step of introducing the compound represented by the formula (I), a salt thereof, or an ester thereof according to claim 3 into a cell, and
   (b) the step of measuring fluorescence emitted by the compound represented by the formula (I) or a salt thereof in the cell.

15. A method for measuring an acidic region in a cell, which comprises the following steps:
   (a) the step of introducing the compound represented by the formula (I), a salt thereof, or an ester thereof according to claim 4 into a cell, and
   (b) the step of measuring fluorescence emitted by the compound represented by the formula (I) or a salt thereof in the cell.

* * * * *